US009085507B2

(12) United States Patent
Fischer et al.

(10) Patent No.: US 9,085,507 B2
(45) Date of Patent: Jul. 21, 2015

(54) DESFESOTERODINE IN THE FORM OF A TARTARIC ACID SALT

(75) Inventors: Dirk Fischer, Frankfurt am Main (DE); Gertraud Koellner, Neu-Ulm (DE); Gertrud Auer, Gomaringen (DE); Katrin Rimkus, Iserlohn (DE); Frank Muskulus, Laupheim (DE); Sandra Brueck, Munich (DE); Jana Paetz, Bonn (DE)

(73) Assignee: ratiopharm GmbH, Ulm (DE)

( * ) Notice: Subject to any disclaimer, the term of this patent is extended or adjusted under 35 U.S.C. 154(b) by 919 days.

(21) Appl. No.: 13/319,746

(22) PCT Filed: May 10, 2010

(86) PCT No.: PCT/EP2010/002858
§ 371 (c)(1),
(2), (4) Date: Jan. 30, 2012

(87) PCT Pub. No.: WO2010/130392
PCT Pub. Date: Nov. 18, 2010

(65) Prior Publication Data
US 2012/0128773 A1    May 24, 2012

(30) Foreign Application Priority Data

May 11, 2009   (EP) .................................... 09006357
May 20, 2009   (EP) .................................... 09006848
Oct. 16, 2009  (EP) .................................... 09013104

(51) Int. Cl.
C07C 215/54   (2006.01)
A61K 31/137   (2006.01)
A61K 9/20     (2006.01)
A61K 9/28     (2006.01)
A61K 9/50     (2006.01)
C07C 59/255   (2006.01)

(52) U.S. Cl.
CPC .............. *C07C 215/54* (2013.01); *A61K 9/2081* (2013.01); *A61K 9/2866* (2013.01); *A61K 9/5047* (2013.01); *A61K 31/137* (2013.01); *C07C 59/255* (2013.01); *C07B 2200/07* (2013.01)

(58) Field of Classification Search
CPC ........................... A61K 31/137; C07C 215/54
See application file for complete search history.

(56) References Cited

U.S. PATENT DOCUMENTS

| | | | | |
|---|---|---|---|---|
| 5,382,600 | A * | 1/1995 | Jonsson et al. ................. | 514/603 |
| 5,559,269 | A * | 9/1996 | Johansson et al. ............ | 564/443 |
| 6,858,650 | B1 | 2/2005 | Meese | |
| 7,005,449 | B2 * | 2/2006 | Hawley et al. ................ | 514/555 |
| 7,985,772 | B2 | 7/2011 | Meese et al. | |

FOREIGN PATENT DOCUMENTS

| | | |
|---|---|---|
| DE | 199 32 651 | 1/2001 |
| EP | 1 077 912 | 2/2001 |
| EP | 1 230 209 | 8/2002 |
| WO | WO 8906644 A1 * | 7/1989 |
| WO | WO 2005/012227 | 2/2005 |
| WO | WO 2007/138440 | 12/2007 |
| WO | WO 2007/141298 | 12/2007 |
| WO | WO 2009057138 A2 * | 5/2009 |

OTHER PUBLICATIONS

Chapple et al. European Urology 2007, 52, 1204-1212.*
FDA, Detrol® LA, NDA 21-228, pp. 1-15, Apr. 2004, obtained from http://www.fda.gov/ohrms/dockets/ac/05/briefing/2005-4152b1_02_05_02_Detrol%20LA%20label%20FDA%204-14-04.pdf on Jan. 18, 2015.*
Pilchik, R. Pharmaceutical Technology, Nov. 2000, pp. 68-78.*
Nilvebrant, L., "Tolterodine and it's Active 5-Hydroxymethyl Metabolite: Pure Muscarinic Receptor Antagonists", Pharmacology and Toxicology, Munksgaard International Publishers, Copenhagen, DK, vol. 90, No. 5, May 1, 2002, pp. 260-267, XP001188936, ISSN: 0901-9928.
International Search Report dated Sep. 16, 2010 for PCT/EP2010/002858.

* cited by examiner

*Primary Examiner* — Matthew Coughlin
(74) *Attorney, Agent, or Firm* — Baker & Hostetler LLP

(57) ABSTRACT

The invention concerns desfesoterodine in the form of a tartaric acid salt, in particular in the polymorphic "R form", as well as a process for its production. In a second aspect, the invention concerns the desfesoterodine of the invention in a microencapsulated form.

15 Claims, 3 Drawing Sheets

DESFESOTERODINE IN THE FORM OF A TARTARIC ACID SALT

CROSS-REFERENCE TO RELATED APPLICATION

This application claims benefit under 35 U.S.C. 371 of International Application No. PCT/EP2010/002858, filed May 10, 2010, and published as International Publication No. WO 2010/130392, the contents of which are incorporated herein by reference in their entirety.

FIELD OF THE INVNETION

The invention relates to desfesoterodine in the form of a tartaric acid salt, in particular in the polymorphic "R form", as well as to a process for its production. In a second aspect, the invention relates to the desfesoterodine of the invention in a microencapsulated form.

BACKGROUND OF THE INVENTION

Fesoterodine is an antimuscarinic for the treatment of overactive bladder syndrome. Treatment with fesoterodine has substantially improved the symptoms of overactive bladder syndrome which patients find extremely stressful. In all clinically relevant outcomes from both phase III studies (2, 3) (urge incontinence results/24 h, micturition frequency, median micturition volume), statistically significant improvements were obtained over placebo. Fesoterodine is currently marketed under the brand name Toviaz®. Fesoterodine is a prodrug. Taken orally, the prodrug is activated by esterases in the human body to the active metabolite.

The IUPAC name for fesoterodine [INN] is 2-[(1R)-3-(diisopropylamino)-1-phenylpropyl]-4-(hydroxymethyl)phenyl-isobutyrate. The chemical structure of fesoterodine is illustrated in formula (1) below:

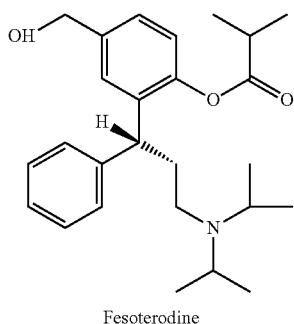

Fesoterodine

Synthesis pathways for fesoterodine can be obtained from EP 1 077 912 B1. Fesoterodine salts are described in EP 1 230 209 B1.

Fesoterodine is not particularly stable to hydrolysis. For this reason, fesoterodine tablet formulations were proposed in WO 2007/141298 which contain fesoterodine in the form of a fumarate or hydrogen fumarate salt and a stabilizer against hydrolysis; the stabilizer is preferably xylitol. However, the use of xylitol in pharmaceutical formulations is usually undesirable. In addition, it has been shown that despite using xylitol, processing the corresponding pharmaceutical formulations is problematic because of hygroscopic properties. In addition, the resulting dosage forms cause problems linked to stability on storage; as an example, they can only be packaged in expensive films with low water vapour permeability.

SUMMARY OF THE INVENTION

Thus, the aim of the present invention is to overcome the disadvantages set out above.

In particular, the aim of the invention is to provide a pharmaceutical active ingredient for the treatment of overactive bladder syndrome which does not have any undesirable hygroscopic properties and can be processed advantageously. In order to guarantee good processability, the active ingredient is prepared in a form which is free-flowing, has good packing ability, is non-hygroscopic and has good compressibility.

A further aim of the invention is to provide a pharmaceutical active ingredient for the treatment of overactive bladder syndrome which has advantageous storage stability in the context of a pharmaceutical formulation. In particular, the advantageous stability on storage should also be obtained when existing films with a medium to high water vapour permeability are used for the packaging.

An additional aim of the invention is to provide a pharmaceutical active ingredient for the treatment of overactive bladder syndrome which has essentially the same solubility as fesoterodine fumarate or fesoterodine hydrogen fumarate and thus is essentially bioequivalent to fesoterodine fumarate or fesoterodine hydrogen fumarate upon oral administration.

The above cited aims can surprisingly be accomplished by using a tartaric acid salt of the fesoterodine metabolite "desfesoterodine" instead of fesoterodine fumarate or fesoterodine hydrogen fumarate, in particular in the polymorphic R form described below.

Thus, the subject matter of the invention concerns a desfesoterodine in the form of a tartaric acid salt as well as a process for the production thereof.

BRIEF DESCRITION OF THE DRAWINGS

DETAILED DESCRIPTION OF THE INVENTION

Desfesoterodine is known in the art and can, for example, be produced in according with WO 2005/012227. Desfesoterodine is a compound with the following structure (2):

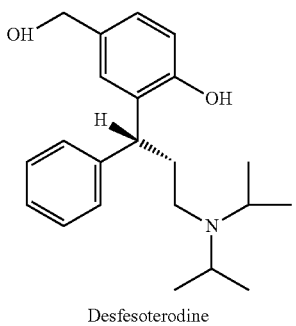

Desfesoterodine

Further, the expression "desfesoterodine" can also encompass enantiomers or racemates of the compound with structure (2). The expression "desfesoterodine" thus describes 2-(3-diisopropylamino-1-phenylpropyl)-4-hydroxymethylphenol, in particular (R)-2-(3-diisopropylamino-1-phenylpropyl)-4-hydroxymethylphenol.

Tartaric acid is also known by specialists as 2,3-dihydroxy succinic acid. In the context of the present invention, tartaric acid can be used as D-(−)-tartaric acid, L-(+)-tartaric acid, meso-tartaric acid or any mixture thereof, for example as the DL racemate.

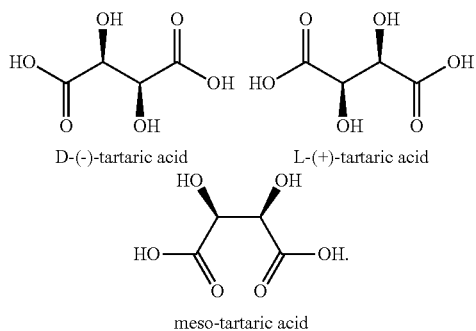

D-(−)-tartaric acid  L-(+)-tartaric acid meso-tartaric acid

In a preferred embodiment, L-(+)-tartaric acid is used.

In the desfesoterodine salt of the invention, the tartaric acid may be present as the doubly (tartrate) or singly (hydrogen tartrate) negatively charged anion. Preferably, the tartaric acid is present as the tartrate. Correspondingly, it is possible for the molar ratio of desfesoterodine to tartaric acid to be 1:1 to 2:1. Preferably, the molar ratio of desfesoterodine to tartaric acid in the desfesoterodine salt of the invention is approximately 1:1.

In principle, the desfesoterodine salt of the invention can, for example, be in the amorphous form, the crystalline form or in the form of a solid solution. Preferably, the desfesoterodine salt of the invention is in the crystalline form.

In a preferred embodiment, the crystalline desfesoterodine salt of the invention is used in the polymorphic "R form".

Figure 1:
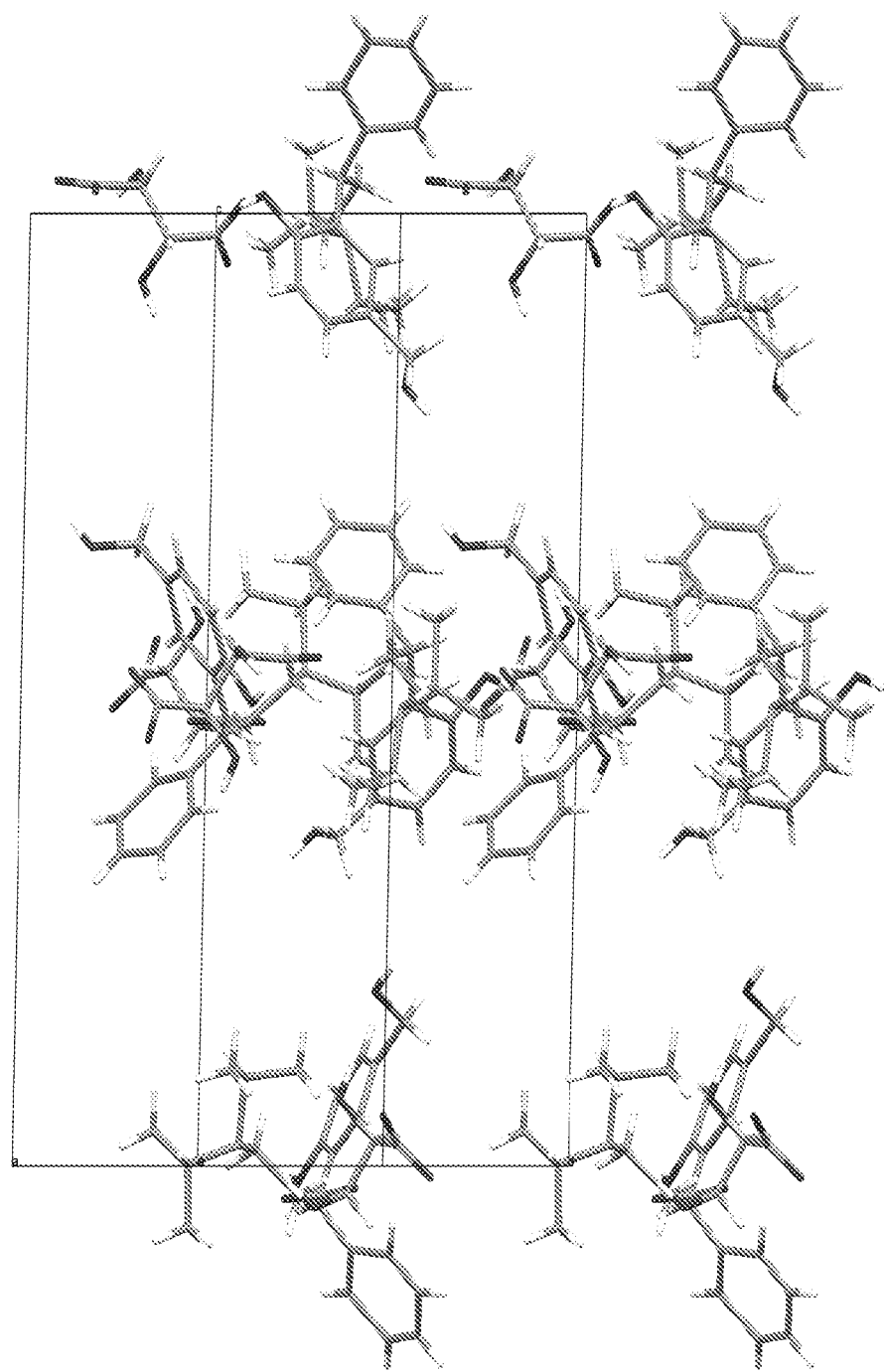
FIG. 1 illustrates the laminar structure of a single crystal of the R form of crystalline desfesoterodine tartaric acid salt.

The crystalline desfesoterodine salt of the invention, in particular the R form of the invention, is characterized herein by a crystalline lattice with a laminar structure. FIG. 1 shows the laminar structure in a single crystal of the R form. Solvent molecules can be embedded between the structures. Unexpectedly, it turns out that a desfesoterodine salt of the invention with a laminar structure in particular advantageously accomplishes the aims set out above.

The crystalline desfesoterodine salt of the invention, in particular the R form of the invention, is preferably in a monoclinic crystal system.

In addition, the R form is defined by the following parameters determined using single crystal analysis:

| Space group: | | $P\,2_1$ |
|---|---|---|
| Lattice parameter: | a | 15.5 Å |
| | b | 11.2 Å |
| | c | 22.5 Å |
| | α | 90° |
| | β | 93.9° |
| | γ | 90° |
| Cell volume V: | | 3899 Å$^3$ |
| Molecules per unit cell Z: | | 4 |

Further, the "R form" of the desfesoterodine salt of the invention is preferably characterized in that in the powder X-ray diffraction diagram (=powder X-ray diffractometry), characteristic reflections occur, on the 2-theta scale using $\lambda=1.54$ Å (Cu K), at approximately $11.7°\pm0.2°$, $18.4°\pm0.2°$ and $18.8°\pm0.2°$. Further characteristic reflections occur, for example, at $16.0°\pm0.2°$, $16.8°\pm0.2°$, $18.6°\pm0.2°$, $20.6°\pm0.2°$, $20.7°\pm0.2°$, $21.8°\pm0.2°$, $22.0°\pm0.2°$, $23.2°\pm0.2°$, $23.6°\pm0.2°$, $24.9°\pm0.2°$ and $29.5°\pm0.2°$.

The powder X-ray diffraction diagrams were obtained in the reflection configuration (Bragg-Brentano-Geometry). The sample carriers were PMMA carriers with a sample volume of 20.0 mm diameter and 1 mm depth. The measurements were recorded using an X-ray source with a copper anode at a generator voltage of 40 kV at 40 mA current with a measuring circle of 435.0 mm. Detection was carried out with a fast, high sensitivity position-sensitive detector (Vantec-1 from Bruker AXS, Karlsruhe).

Figure 2:
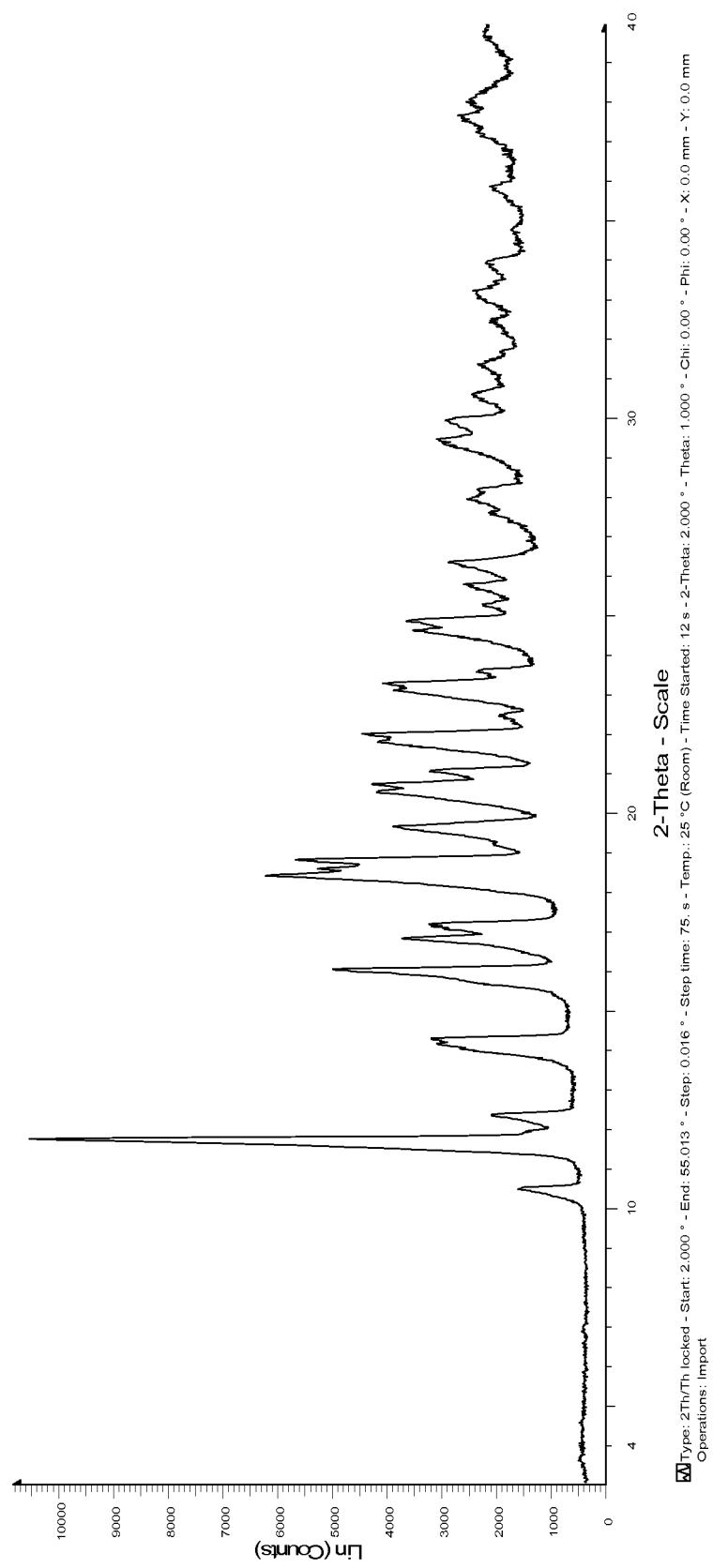
FIG. 2 illustrates a powder X-ray diffractogram of the polymorphic R form of desfesoterodine tartaric acid salt.

A powder X-ray diffractogram (hereinafter denoted "XRPD") of the polymorphic R form is shown in FIG. 2. Thus, the subject matter of the invention is a desfesoterodine tartaric acid salt characterized by XRPD, in accordance with FIG. 2.

The crystalline desfesoterodine salt of the invention, in particular the R form of the invention, preferably has a melting point of approximately 166° C. to 170° C. The melting point is preferably determined using a Buechi® Melting Point B-545 apparatus (with thermodynamic correction).

The desfesoterodine alts of the invention are preferably (in particular having regard to processability and bioequivalence) in the form of a particulate composition wherein the mean particle diameter (D50) is usually 1 μm to 500 μm, preferably 5 μm to 350 μm, more preferably 10 μm to 300 μm, particularly preferably 20 μm to 250 μm, in particular 50 μm to 200 μm.

Unless otherwise indicated, the expression "mean particle diameter" in the context of the present invention refers to the D50 value of the mean volumetric particle diameter, which is determined by laser diffractometry. In particular, a Mastersizer 2000 from Malvern Instruments is used for the determination (moist measurement, 2000 rpm, liquid paraffin as the dispersing agent, 60 seconds ultrasound, evaluation using the Fraunhofer method). The mean particle diameter, also known as the D50 value for the integral volume distribution, is defined in the context of the present invention as the particle diameter for which 50% by weight of the particles have a diameter smaller than the diameter corresponding to the D50 value. Similarly, 50% by weight of the particles have a diameter larger than the D50 value.

The subject matter of the present invention not only concerns the tartaric acid salts of desfesoterodine in accordance with the invention, but also a process for its production. The process of the invention for the production of the tartaric acid salts of desfesoterodine described in the present application comprises the following steps:
(i) dissolving desfesoterodine in a first solvent;
(ii) dissolving tartaric acid in a second solvent;
wherein the first and the second solvents preferably have a polarity of 0.4 to 1.0 measured at 20° C.;
(iii) combining the solutions from steps (i) and (ii);
(iv) allowing the desfesoterodine to crystallize in the form of the tartaric acid salt, if necessary by cooling the solution from step (iii) to temperatures of −50° C. to 15° C.

In principle, the above discussion relating to the preferred embodiments also apply to the process of the invention; as an example, L-(+)-tartaric acid is also particularly preferably employed in the process of the invention.

In the first step (i) of the process, desfesoterodine (for example desfesoterodine in accordance with Example 1 of WO 2005/012227) is dissolved in a first solvent, preferably completely dissolved. The expression "solvent" in this context also encompasses mixtures of solvents.

In the second step (ii) of the process, tartaric acid is dissolved in a second solvent, preferably completely dissolved. The expression "solvent" in this context also encompasses mixtures of solvents.

The same or even different solvents may be used in step (i) and (ii). Preferably, the same solvent is used. In a preferred embodiment, the first and the second solvents have a polarity (measured at 20° C.) of 0.3 to 0.9, in particular 0.4 to 0.7.

Examples of suitable solvents are ethyl acetate (0.58), tetrahydrofuran (0.45), acetonitrile (0.65), isopropanol (0.82), acetone (0.56) and 2-butanone (0.51). Tetrahydrofuran (THF) or 2-butanone are particularly preferred.

The table below summarizes the polarities of the usual solvents (eluotropic series).

TABLE 1

| Active ingredient | Polarity |
| --- | --- |
| Fluoroalkane | −.25 |
| n-Hexane | 0.00 |
| Petroleum ether | 0.01 |
| Cyclohexane | 0.04 |
| Xylene | 0.26 |
| Isopropyl ether | 0.28 |
| Isopropyl chloride | 0.29 |
| Toluene | 0.29 |
| Chlorobenzene | 0.30 |
| Benzene | 0.32 |
| Ethyl bromide | 0.37 |
| Diethyl ether | 0.38 |
| Ethyl sulphide | 0.38 |
| Chloroform | 0.40 |
| Dichloromethane | 0.42 |
| Methyl-isobutylketone | 0.43 |
| Tetrahydrofuran | 0.45 |
| Ethylene dichloride | 0.49 |
| Butanone | 0.51 |
| Nitropropane | 0.53 |
| Acetone | 0.56 |
| Dioxane | 0.56 |
| Ethyl acetate | 0.58 |
| Methyl acetate | 0.60 |
| Amyl alcohol | 0.61 |
| Aniline | 0.62 |
| DMSO | 0.62 |
| Diethylamine | 0.63 |
| Nitromethane | 0.64 |
| Acetonitrile | 0.65 |
| Pyridine | 0.71 |
| Isopropanol/n-Propanol | 0.82 |
| Ethanol | 0.88 |

TABLE 1-continued

| Active ingredient | Polarity |
| --- | --- |
| Methanol | 0.95 |
| Ethylene glycol | 1.11 |

In the third step (iii) of the process, the solutions from step (i) and step (ii) are combined. Preferably, the solution from step (ii) is added to the solution from step (i), in particular by dropping it in. In an alternative embodiment, the steps (i) to (iii) may also be carried out simultaneously in a reaction vessel.

In a preferred embodiment, steps (i) to (iii) are carried out at a temperature of the solvent of 20° C. to 80° C., preferably 40° C. to 75° C.

In the fourth step (iv) of the process, the desfesoterodine is allowed to crystallize in the form of a tartaric acid salt, preferably in the R form. The exact crystallization conditions (temperature, time) depend on the choice of solvent. In a preferred embodiment, crystallization is carried out by cooling the solution from step (iii) to temperatures of −80° C. to 20° C., more preferably −50° C. to 15° C., in particular −10° C. to 10° C.

In an alternative embodiment, the desfesoterodine may be allowed to crystallize in the form of the tartaric acid, preferably in the R form, by adding a third solvent (or solvent mixture). In a preferred embodiment, the third solvent has a polarity (measured at 20° C.) of 0.0 to 0.4, in particular 0.01 to 0.29. Examples of suitable solvents are n-hexane (0.00), cyclohexane (0.04), n-heptane (0.01), ligroin, petroleum ether fractions (0.01), methyl-tert-butyl ether (0.28) and isopropyl ether (0.28).

In the optional step (v) of the process, the resulting desfesoterodine is dried in the form of a tartaric acid under reduced pressure. The drying conditions (in particular drying time and pressure) are preferably selected so that the resulting desfesoterodine in the form of the tartaric acid salt has a residual solvent content of less than 3.0% by weight (i.e. between 0.0001 and 3.0% by weight, for example), more preferably less than 2.0% by weight, still more preferably less than 1.0% by weight and particularly preferably less than 0.5% by weight, in particular less than 0.1% by weight. Normally in this regard, a pressure of 0.1 to 0.8 bar, preferably 0.2 to 0.5 bar is used. The drying time normally lasts 0.1 to 10 hours, preferably 1 to 5 hours.

Drying the desfesoterodine salts of the invention, in particular in the R form, for example to the residual solvent contents mentioned above, surprisingly occurs without destruction of the crystalline lattice.

Thus, the subject matter of the invention concerns all of the crystalline tartaric acid salts of desfesoterodine described herein, characterized in that they have a residual solvent content of less than 3.0% by weight (i.e. between 0.0001 and 3.0% by weight, for example), more preferably less than 2.0% by weight, still more preferably less than 1.0% by weight and particularly preferably less than 0.5% by weight, in particular less than 0.1% by weight. The residual solvent content is preferably determined using gas chromatography, in particular using a Perkin Elmer Clarus 500 system, preferably in accordance with USP 467.

In a preferred embodiment, the desfesoterodine salt of the invention, in particular in the R form, also has a water content of 0.01% to 4.0% by weight, preferably 0.02% to 2.0% by weight, more preferably 0.05% to 1.5% by weight, still more preferably 0.10% to 1.0% by weight, in particular 0.15% to 0.9% by weight. The residual water content is determined using the Karl Fischer Method, which employs a coulometer at 160° C. Preferably, a Metrohm 831 KF Coulometer is used with a diaphragmless titration cell. Normally, a 20 mg sample of desfesoterodine salt is analyzed. A desfesoterodine salt with the defined water content surprisingly advantageously accomplishes the aims described above.

The desfesoterodine salt of the invention, in particular in the R form, is normally used for the production of a pharmaceutical formulation. Thus, the subject matter of the invention concerns a pharmaceutical formulation containing the desfesoterodine salt of the invention, in particular in the R form, as well as pharmaceutical excipients. These are excipients which are known to the skilled person, for example those described in the European Pharmacopoeia.

The inventors of the present application have also surprisingly established that the desfesoterodine salt of the invention, in particular in the R form, has an almost identical in vitro solubility profile to that of fesoterodine fumarate. In contrast, the desfesoterodine fumarate which is known from the prior art has a substantially poorer in vitro solubility profile.

Thus, the subject matter of the invention concerns the use of desfesoterodine in the form of a tartaric acid salt for the production of a pharmaceutical formulation which when taken orally is essentially bioequivalent to a corresponding pharmaceutical formulation with fesoterodine fumarate or fesoterodine hydrogen fumarate.

In principle, the above discussions relating to preferred embodiments also apply to the use in accordance with the invention; as an example, L-(+)-tartaric acid is also particularly preferably employed in the use of the invention. Equally, the salt of the invention is preferably used in the polymorphic R form.

The expression "in a corresponding pharmaceutical formulation" in this context means that the formulation of the invention (containing desfesoterodine in the form of a tartaric acid salt) is essentially bioequivalent to a comparative formulation (containing fesoterodine fumarate or fesoterodine hydrogen fumarate) with essentially the same galenical formulation.

The expression "essentially bioequivalent" in this context means that the plasma concentration-time profiles for both formulations at the same dose are so similar that, having regard to therapeutically desired or unwanted effects, no clinically relevant differences can be expected. The bioequivalence was tested using the in vivo bioavailabilty parameters AUC, $c_{max}$ and $t_{max}$. The expressions "AUC", "$c_{max}$" and "$t_{max}$" are known in the art and are explained in Bauer, Frömming, Führer, "Lehrbuch der pharmazeutischen Technologie" ["Pharmaceutical Technology Textbook"], $8^{th}$ Edition, pp 207-214.

Preferably, the desfesoterodine of the invention in the form of a tartaric acid salt or the pharmaceutical formulation of the invention containing desfesoterodine in the form of a tartaric acid salt, when taken orally, results in an AUC value which is 90% to 110%, more preferably 95% to 105% of the AUC value which is obtained upon oral administration of a corresponding pharmaceutical formulation with the same quantity of active ingredient fesoterodine fumarate or fesoterodine hydrogen fumarate. Similarly, a $t_{max}$ is preferably targeted which is 90% to 110%, more preferably 95% to 105% of the $t_{max}$ value which would be obtained upon oral administration of a corresponding pharmaceutical formulation with the same quantity of the active ingredient fesoterodine fumarate or fesoterodine hydrogen fumarate. In addition, a $c_{max}$ is preferably targeted which is 90% to 110%, more preferably 95% to 105% of the $c_{max}$ value which would be obtained upon oral administration of a corresponding pharmaceutical formulation with the same quantity of the active ingredient fesoterodine fumarate or fesoterodine hydrogen fumarate.

Consequently, the present invention overcomes the disadvantages of fesoterodine fumarate or fesoterodine hydrogen fumarate (difficult to process, problematic stability on storage) mentioned above, essentially without altering the galenical formulation.

Furthermore, using fesoterodine fumarate or fesoterodine hydrogen fumarate—as discussed above—can occasionally require expensive packaging with a particularly low water vapour permeability. As an example, a PVC-CTFE film (polyvinyl chloride—chlorotrifluoroethylene, commercially available as Aclar®) has a particularly low water vapour permeability. However, from a technical viewpoint, it is also desirable to be able to use less expensive packaging means. In the context of the present invention, it was surprisingly discovered that even when cheaper packaging substances were used, a pharmaceutical dosage form for the treatment of overactive bladder syndrome could be prepared which had good stability on storage. Thus, the subject matter of the invention concerns the use of a film with a water vapour permeability of 0.1 $g/m^2d$ to 2.0 $g/m^2d$, preferably with a water vapour permeability of 0.2 $g/m^2d$ to 1.0 $g/m^2d$, in particular with a water vapour permeability of 0.3 $g/m^2d$ to 0.8 $g/m^2d$ for the packaging of a pharmaceutical dosage form containing desfesoterodine, preferably in the form of a tartaric acid. Preferably, the desfesoterodine dosage form in this case is for oral administration.

The water vapour permeability is determined in the context of the present invention in accordance with Kassis et al., Pharm. Ind. 43, 1036 (1981). The parameter "d" means "day".

In a second aspect, the invention concerns an advantageous formulation of the desfesoterodine tartaric acid salt of the invention. In the prior art, in order to formulate fesoterodine, so-called matrix tablets are usually used. The problem with matrix tablets is that frequently, a substantial portion of the active ingredient (approximately 20%) is usually not released. Thus, one aim of the present invention is to provide a dosage form with modified release, wherein release of the active ingredient is as complete as possible.

Prior art manufacturing processes have a preference for conventional wet granulation procedures. In this case, the active ingredient is generally brought into contact with solvents for a lengthy period. However, because of the sensitivity of the active ingredient, this should be avoided.

Fesoterodine is used to treat overactive bladder syndrome. This indication requires that patients should always have their medication with them. However, Toviaz® tablets, which are currently on the market, are only stable on storage up to 25° C. This is unsatisfactory, in particular in the summer months. A further aim of the invention, therefore, is to provide fesoterodine in a form which is suitable for a formulation which in practice is stable on storage at up to 30° C.

An additional aim of the invention is to provide a pharmaceutical active ingredient for the treatment of overactive bladder syndrome, which essentially has the same solubility as the formulations described in WO 2007/141298, in particular the sample formulations listed in Table 1, and thus is essentially bioequivalent thereto for oral administration.

Unexpectedly, the above aims can be achieved by microencapsulating desfesoterodine in the form of the tartaric acid salt. In general, all of the statements made herein regarding the preferred embodiments of the desfesoterodine tartaric acid salt are also applicable to this second aspect of the invention.

Thus, the subject matter of the second aspect of the invention is a pharmaceutical intermediate containing microencapsulated desfesoterodine in the form of a tartaric acid salt.

Figure 3:
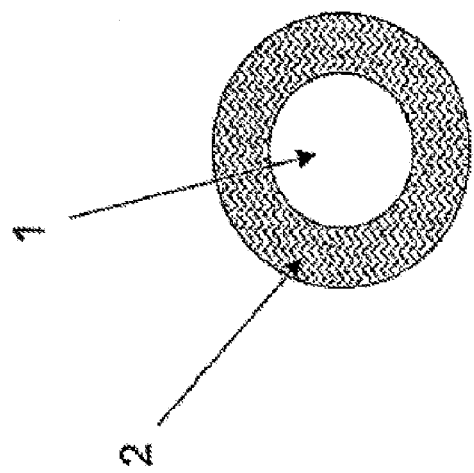
FIG. 3 illustrates a microencapsulated desfesoterodine tartaric acid salt.

The microencapsulated desfesoterodine tartaric acid salt of the invention is illustrated in FIG. 3. FIG. 3 shows:
1 particles of the active ingredient containing desfesoterodine tartaric acid salt;
2 shell.

Figure 4:
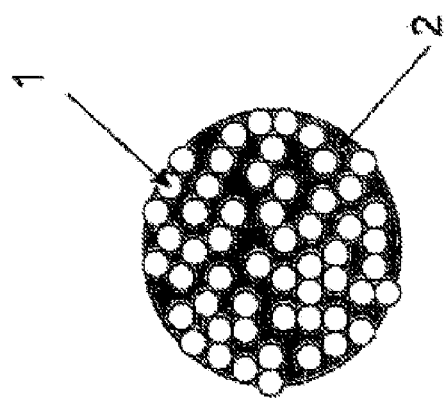
FIG. 4 illustrates a comparative example of microspherules embedded in a polymer matrix without the formation of a capsule shell.

The pharmaceutical intermediate of the invention, however, concerns so-called "microspherules". In contrast to the microcapsules, the active ingredient in microspherules is embedded in a polymer matrix without the formation of a capsule shell. For comparison, microspherules which are not in accordance with the invention are illustrated in FIG. 4. FIG. 4 shows:
1 particles of active ingredient containing fesoterodine;
2 matrix.

Thus, the subject matter of the invention is a pharmaceutical intermediate constructed from a core (a) and a shell (b), wherein
(a) the core contains desfesoterodine tartaric acid salt as the active ingredient; and
(b) the shell contains one or more pharmaceutical excipients which modify the release of the active ingredient. The core (a) contains the active ingredient, preferably in a particulate form, i.e. the core is preferably formed from particles of active ingredient, in particular one or more particles of active ingredient. In addition, the core may also include pharmaceutical excipients in addition to the desfesoterodine tartaric acid salt.

In the context of the present invention, it is of particular advantage for the core to be completely encased/encapsulated. In the context of the present invention, however, the term "encased" or "encapsulated" also encompasses the case in which at least 70%, more preferably at least 80%, particularly preferably at least 90% of the surface of the core is encased.

In general, the core contains desfesoterodine tartaric acid salt as the active ingredient. Preferably, the core essentially consists of a desfesoterodine tartaric acid salt. The term "essentially" as used herein indicates that the core may also contain small amounts of moisture, solvents, pharmaceutical excipients, etc.

Preferably, a desfesoterodine tartaric acid salt with a water content of 0.1% to 5% by weight, more preferably 0.3% to 3% by weight is used in the core.

In a preferred embodiment, the core contains a desfesoterodine tartaric acid salt in a granulated or compressed form. This means that preferably, a core (a) is produced by granulation or compression of the desfesoterodine tartaric acid salt, optionally in the presence of pharmaceutical excipients. Compression is preferable, for example by using an eccentric press. When an eccentric press is used, a force of pressure of 1 to 20 kN is usually used, preferably 2.5 to 10 kN.

In the case of granulated or compressed cores (a), these preferably have a mass average particle size of 0.1 to 4 mm, more preferably 0.5 to 3.5 mm, still more preferably 1.0 to 3.0 mm, in particular 1.5 to 2.5 mm. In the context of this application, the mass average particle size was determined by sieve analysis (preferably using a Retsch® AS 2000). This provides the D50 value.

In the case of granulated or compressed cores (a), in addition to a desfesoterodine tartaric acid salt, they may also contain pharmaceutical excipients. In general, in this regard they will be drawn from the pharmaceutical excipients described below. Preferably, the cores (a) also contain lubricants and/or additives to improve flowability. Particularly preferably, the cores (a) contain:
90% to 100% by weight, in particular 92.0% to 99.0% by weight of desfesoterodine tartaric acid salt;
0 to 10% by weight, in particular 0.5% to 4% by weight of additives to improve flowability;
0 to 10% by weight, in particular 0.5% to 4% by weight of lubricant;
with respect to the total weight of the core (a).

The shell (b) contains or consists of one or more pharmaceutical excipient(s), which modify release of the active ingredient. The shell (b) in this case is preferably a single layer, i.e. the shell is preferably not produced from at least two layers. The term "modified release" as used in the context of the present invention means delayed release, repeat action release, prolonged release, sustained release or extended release. Prolonged release is preferable.

In a preferred embodiment, the shell (b) comprises the components
(b1) a substance which is not soluble in water; and
(b2) a pore-forming agent.

Alternatively, the shell (b) essentially consists of the components (b1) and (b2).

Component (b1) is preferably a polymer which is not soluble in water or a substance with polymer-like properties which is not soluble in water.

The expression "not soluble in water" as used in the context of the present invention means that the substance has a solubility in water of less than 10 mg/L, measured at 25° C. Preferably, the substance which is not soluble in water has a solubility of 8 mg/L or less, in particular 0.01 to 5 mg/L (determined using column elution methods in accordance with EU-Guideline RL67-548-EWG, Annex V, Chapter A6).

The polymer which is not soluble in water (b1) usually has a mass average molecular weight of 50000 to 2500000 g/mole, preferably 150000 to 2000000 g/mole, more preferably 350000 to 1500000 g/mole.

Examples of suitable polymers which are not soluble in water are polymers based on acrylates, for example acrylates, methacrylates; cellulose derivatives such as ethyl cellulose (EC), methyl cellulose (MC), cellulose acetyl phthalate, hydroxypropylmethyl cellulose phthalate; synthetic polymers such as polyvinyl alcohol and derivatives thereof, polyvinyl acetate, polyvinyl chloride, nylon, polyamide, polyethylene and poly(lactide-co-glycolide). In addition, mixtures of the cited polymers are possible.

Particularly preferably, ethyl cellulose is used as the polymer (b1) which is not soluble in water. Ethyl cellulose can, for example, be used in the form of the commercially available Aquacoat® ECD system (FMC BioPolymer, approximately 24.5% to 29.5% ethyl cellulose in aqueous solution).

Waxes and fats may be used as the substances which are not soluble in water (with polymer-like properties. Suitable waxes or fats are solid at 25° C. Suitable examples are solid paraffin or beeswax. Examples of suitable fats are glycerol monostearate and glycerol palmitostearate. In addition, mixtures may be used. Further, mixtures containing polymers which are not soluble in water and substances which are not soluble in water with polymer-like properties may be used.

In addition to the substance which is not soluble in water (b1), the shell (b) also comprises a pore-forming agent (b2). A pore-forming agent is in general a substance which is soluble in water and which dissolves when the shell (b) comes into contact with water, so that water can penetrate into the pores that are formed. The pore-forming agent preferably has a water solubility of 100 mg/L at a temperature of 25° C., particularly preferably more than 250 mg/L.

In principle, two preferred embodiments of the pore-forming agents are possible.

Firstly, the pore-forming agent may be a water soluble polymer (b2-1). Secondly, the pore-forming agent may be a water soluble salt. (b2-2).

Suitable water soluble polymers preferably have hydrophilic groups. Examples of suitable hydrophilic groups are hydroxyl, ether, ester and amino groups. Further, the hydrophilic polymer used for the production of the intermediate preferably has a mass average molecular weight of 1000 to 90000 g/mole, more preferably 2000 to 50000 g/mole.

If the polymer (b2-1) used as the pore-forming agent is dissolved in water in a quantity of 2% by weight, the resulting solution preferably has a viscosity of 0.1 to 8 mPa/s, more preferably 0.5 to 7 mPa/s, in particular 1 to 6 mPa/s, measured at 25° C.

The intermediate of the invention may comprise the following hydrophilic polymers as pore-forming agents, for example: polysaccharides such as hydroxypropylmethyl cellulose (HPMC), methyl cellulose, hydroxyethyl cellulose, ethylhydroxyethyl cellulose, hydroxypropyl cellulose (HPC); polyvinyl pyrrolidone, polyalkylene glycol, such as polypropylene glycol or, as is preferable, polyethylene glycol, polyethylene glycol block copolymers, in particular block copolymers formed from polyethylene glycol and polypropylene glycol (Pluronic®, BASF), as well as mixtures of said polymers.

Preferably, polyethylene glycol is used, in particular with a mass average molecular weight of 2000 to 10000 g/mole.

Alternatively, the pore-forming agent may be a water soluble salt (b2-2). Pharmaceutically acceptable inorganic salts are preferred. Examples of suitable salts are NaCl, KCl and $Na_2SO_4$.

In principle, mixtures of said pore-forming agents are also possible.

The shell (b) may consist of components (b1) and (b2). In a preferred embodiment, in addition to the substance which is not soluble in water (b1) and the pore-forming agent (b2), the shell also contains a polymer with a pH-dependent solubility in water (b3) and/or a plasticizer (b4).

Preferably, the component (b3) is a polymer which has a poorer water solubility at acid than at neutral or alkaline pHs. The polymers (b3) normally have a number average molecular weight of >10000 to 90000, preferably 20000 to 70000 g/mole. Examples of suitable polymers with pH-dependent solubility in water are cellulose acetate trimellitate (CAT), polyvinyl acetate phthalate, hydroxypropylmethyl cellulose phthalate (HPMCP), in particular with a mass average molecular weight of 40000 to 60000, carboxymethylethyl cellulose (CMEC), polyvinylacetate phthalate (PVAP), anionic methacrylates (for example Eudragit® L30), cellulose acetate phthalate (PVAP) and shellac.

In principle, polymers may also be envisaged which fall within the definition of (b2) and also of (b3). However, in the context of the present invention, a polymer is used either as a component (b2) or as a component (b3) alone.

As described above, in a preferred embodiment, the shell also contains a plasticizer as component (b4). The term "plasticizer" generally means substances which can reduce the glass transition temperature of the polymer which is not soluble in water (b1) (i.e. a mixture of (b1) and (b4) has a lower glass transition temperature than component (b1) alone).

Examples of suitable plasticizers are glycerin, citrates such as triethyl citrate, tributyl citrate, acetyl citrate, phthalates such as dibutyl phthalate, diethyl phthalate, dimethyl phthalate, or sebacates such as dibutyl sebacate or diethyl sebacate.

Similarly, alkylene glycols such as ethylene glycol, propylene glycol, butylene glycol (1,4-butanediol) or polyalkylene glycols such as polyethylene glycol, preferably with a mass average molecular weight of 300 to 1500 g/mole, may be used. Preferably triethyl citrate and/or dibutyl sebacate are used; in particular, triethyl citrate is used as the plasticizer (b4). Mixtures of the cited plasticizers may also be used.

The shell (b) preferably contains 70% to 99% by weight, more preferably 75% to 95% by weight, particular preferably 80% to 93% by weight, in particular 85% to 92% by weight of polymer which cannot be dissolved in water (b1).

The shell (b) also preferably contains 1% to 20% by weight, more preferably 2% to 15% by weight, particularly preferably 3% to 12% by weight of pore-forming agent (b2).

In addition, the shell (b) preferably contains 0 to 20% by weight of polymer with a pH-dependent solubility (b3).

In addition, the shell (b) preferably contains 0 to 20% by weight, more preferably 2% to 15% by weight, particularly preferably 3% to 12% by weight of a plasticizer (b4).

The cited individual ranges can be combined in any manner. By way of example, the shell (b) may contain (b1) 75% to 95% by weight, more preferably 80% to 90% by weight of water-insoluble polymer;

(b2) 0.1% to 20% by weight of pore-forming agent, more preferably 0.5% to 15% by weight, in particular 0.1% to 10% by weight; and (b3) 0 to 20% by weight of polymer with a pH-dependent solubility; and/or (b4) 0 to 20% by weight, more preferably 2% to 15% by weight, in particular 3% to 12% by weight of plasticizer;

with respect to the total weight of the shell (b).

More preferably, the shell (b) essentially consists of the components (b1), (b2) and (b4).

The quantities of the core (a) and shell (b) employed are preferably selected so that the core is completely encased. Thus, the core is preferably completely encapsulated.

The intermediate of the invention is preferably in the form of a particulate composition, wherein the mass average particle size is 0.15 to 5 mm, 0.6 to 4.0 mm, still more preferably 1.5 to 3.3 mm, in particular 1.8 to 2.8 mm. As described above, the mass average particle size is determined by sieve analysis. The second embodiment is preferably used when the cores (a) are granulated or compressed, as described above.

Normally, in the intermediate of the invention, the weight ratio of core (a) to shell (b) is 15:1 to 1:5, preferably 10:1 to 1:3, more preferably 8:1 to 1:2, in particular 6:1 to 1:1. The second embodiment is preferably used when the core (a) is granulated or compressed as described above.

The intermediate of the invention (i.e. the microencapsulated desfesoterodine tartaric acid salt) is in general produced by a process wherein the polymer shell is applied to the desfesoterodine tartaric acid salt core.

Thus, the invention concerns a process for the production of the pharmaceutical intermediate of the invention, comprising the following steps:

(i) preparing a desfesoterodine tartaric acid salt in a particulate form;

(ii) preparing a solution which contains shell-forming pharmaceutical excipients;

(iii) spraying the solution from step (ii) onto the particles of the desfesoterodine tartaric acid salt; and (iv) removing the solvent.

Preferably, in step (i) of the process of the invention, the desfesoterodine tartaric acid salt is used with a mass average particle size of 0.1 to 4 mm, more preferably 0.5 to 3.5 mm, still more preferably 1.0 to 3.0 mm, in particular 1.5 to 2.5 mm In step (ii), pharmaceutical excipients suitable for forming the shell (b) are dissolved or suspended in a solvent or solvent mixture, preferably completely dissolved. In particular, said pharmaceutical excipients are the components (b1), (b2), (b3) and/or (b4) discussed above. The above discussion relating to the intermediate of the invention may also be used in the process of the invention.

Examples of suitable solvents are water, alcohol (for example methanol, ethanol, isopropanol), dimethylsulphoxide (DMSO), acetone, butanol, ethyl acetate, heptane, pentanol or mixtures thereof. Preferably, an ethanol/water mixture or, in particular, water is used. The shell-forming substances, preferably the components (b1), (b2) and possibly (b3) and/or (b4), are normally present in the solution/suspension in a concentration of 5% to 95% by weight, preferably 60% to 90% by weight, with respect to the total weight of the solution.

In the next step (iii), the solution from step (ii) is sprayed onto the desfesoterodine tartaric acid salt particles. Preferably, spraying is carried out in a fluidized bed.

In step (iv), the solvent is removed, preferably completely removed. Preferably, the solvent is removed by means of high temperature and/or low pressure. The residual solvent content in the shell (b) is preferably less than 2% by weight.

Preferably, steps (i) to (iv) are carried out in a single procedure, preferably in one machine. The residence time for the solvent on the active ingredient should be as short as possible, preferably less than 10 minutes, in particular less than 5 minutes.

In a preferred embodiment, the process of the invention is carried out in a fluidized bed granulator, for example in a Glatt® GPCG 3 (Glatt GmbH, Germany).

In addition to the process described above, intermediates obtainable by the process of the invention also constitute the subject matter of the invention.

The intermediate of the invention (i.e. the encapsulated desfesoterodine tartaric acid salt of the invention) is normally used for the production of a pharmaceutical formulation.

Thus, the invention concerns a pharmaceutical formulation containing an intermediate in accordance with the invention as well as pharmaceutical excipients.

The excipients in this case are known to the skilled person, for example those described in the European Pharmacopeia.

The ratio of active ingredient to excipients is preferably selected so that the resulting formulations contain: 0.1% to 50% by weight, more preferably 0.5% to 40% by weight, still more preferably 1% to 30% by weight, in particular 2% to 20% by weight of desfesoterodine tartaric acid salt; and 50% to 99.9% by weight, 60% to 99.5% by weight, more preferably 70% to 99% by weight, in particular 80% to 98% by weight of pharmaceutically acceptable excipients.

In these figures, the quantity of shell substance (b) and, if appropriate, also the quantity of excipients in the core (a) used for the production of the intermediate of the invention, is included in the excipient. This means that the quantity of active ingredient is with respect to the quantity of desfesoterodine tartaric acid salt contained in the formulation.

Examples of the excipients used are disintegrating agents, anti-caking agents, pseudo-emulsifiers, fillers, additives for improving powder flowability, release agents, wetting agents and/or lubricants.

The formulation of the invention may contain fillers. The term "fillers" generally means substances which serve to form the body of the tablets when those tablets contain small amounts of active ingredients. This means that fillers "stretch" the active ingredients into a sufficient tablet mass. Fillers thus usually serve to produce a suitable tablet size.

Examples of preferred fillers are lactose, lactose derivatives, starch, starch derivatives, treated starch, talc, calcium phosphate, saccharose, calcium carbonate, magnesium carbonate, magnesium oxide, calcium sulphate, hydrogenated vegetable oil and kaolin. In addition, siliconized microcrystalline cellulose (for example Prosolv®, Rettenmaier & Söhne, Germany) may be used. The preferred siliconized microcrystalline cellulose is commercially available and has a silicon dioxide content of 1% to 3% by weight, preferably 2% by weight. In addition, combinations of the cited fillers may be used; as an example, a combination of lactose and microcrystalline cellulose may advantageously be used.

The fillers are usually used in a quantity of 1% to 90% by weight, more preferably 10% to 80% by weight, more preferably 20% to 60% by weight, with respect to the total weight of the formulation.

In general, "disintegrating agents" means substances which accelerate disintegration of a dosage form, in particular a tablet, after immersion in water. Examples of suitable disintegrating agents are organic disintegrating agents such as carragheenan, croscarmellose and crospovidone. Alternatively, alkaline disintegrating agents may be used. The term "alkaline disintegrating agents" means disintegrating agents which, when dissolved in water, have a pH of more than 7.0, for example $NaHCO_3$ or $Na_2CO_3$.

Disintegrating agents are usually used in a quantity of 0 to 20% by weight, more preferably 1% to 15% by weight, in particular 2% to 10% by weight, with respect to the total formulation weight. When granulated or compressed cores (a) are used, then preferably, no disintegrating agents are used.

An example for the additive for improving powder flowability is dispersed silicon dioxide, for example that known by the trade name Aerosil®. Preferably, silicon dioxide with a specific surface area of 50 to 400 $m^2/g$ is used, determined by gas adsorption in accordance with Ph Eur, $6^{th}$ edition, 2.9.26, in particular when granulated or compressed cores (a) are used.

Additives for improving powder flowability are usually used in a quantity of 0.1% to 3% by weight with respect to the total formulation weight.

Further, lubricants may be used. Lubricants are generally used to reduce friction. In particular, the friction which arises when making tables, on the one hand between the die moving to and fro in the die bore and the die wall, and on the other hand between the tablet stage and the die wall, should be reduced. Examples of suitable lubricants are stearic acid, adipic acid, sodium stearyl fumarate (Pruv®) and/or magnesium stearate.

Lubricants are usually employed in a quantity of 0.1% to 3% by weight with respect to the total formulation weight.

Further, anti-caking agents may be used. The term "anti-caking agents" should usually be understood to mean substances which prevent agglomeration in the core bed. Examples are talc, silica gel and/or glycerol monostearate. The anti-caking agents are usually employed in a quantity of 0 to 3% by weight with respect to the total formulation weight.

The nature of pharmaceutical excipients is such that to some extent they can fulfil several functions in a pharmaceutical formulation. In the context of the present invention, then, for the purposes of unambiguous delimitation, it is assumed that a substance which is used as a specific excipient is not simultaneously also used as another type of pharmaceutical excipient. As an example, microcrystalline cellulose—when used as a filler—is not also used as a disintegration agent (although microcrystalline cellulose also has a certain disintegrating effect).

An advantage of the present invention is that moisture stabilizers can be dispensed with. The formulation of the invention preferably does not contain any humectants selected from glucose, glucose derivatives and sugar alcohols. Particularly preferably, the formulation of the invention contains no isomalt, xylitol, sorbitol, polydextrose, dextrose and mixtures thereof.

The formulation of the invention can be administered in various dosage forms. Preferably, it is pressed into tablets. Alternatively, the formulation of the invention can be made into capsules, sachets or stick-packs.

Preferably, the pharmaceutical formulation of the invention is used in the form of tablets. Thus, the invention concerns a process for the production of a tablet containing the pharmaceutical formulation of the invention, comprising the following steps:

(a) mixing the intermediate of the invention with pharmaceutical excipients;
(b) pressing to form tablets, if appropriate with the addition of further pharmaceutical excipients; and
(c) if appropriate, coating the tablets.

In step (a), the intermediate of the invention and further (as described above) pharmaceutical excipients are mixed. Mixing may be carried out in the usual mixers. As an example, mixing may be carried out in compulsory mixers or gravity mixers (for example using a Turbula® T10B (Bachofen AG, Switzerland)). The mixing time may be 1 to 15 minutes, for example.

In step (b), compression into tablets is carried out. The compression may be carried out in tablet making machines which are known in the art. Preferably, compression is carried out in the absence of solvents.

Examples of suitable tablet making machines are eccentric presses or rotary presses. As an example, a Fette 102i (Fette GmbH, Germany) may be used. If a rotary press is used, a compressive force of 2 to 40 kN is usually applied, preferably 2.5 to 35 kN. In the case of eccentric presses, a compressive force of 1 to 20 kN is applied, preferably 2.5 to 10 kN. As an example, a Korsch® EK0 is used.

In the optional step (c) of the process of the invention, the tablets from step (b) are coated. To this end, processes for coating tablets that are known in the art may be employed.

Preferably, macromolecular substances are used for coating, for example modified celluloses, polymethacrylates, polyvinyl pyrrolidone, polyvinylacetate phthalate, zein and/or shellac.

The thickness of the coating layer is preferably 10 to 100 μm.

Preferably, the optional applied film has essentially no effect on release. Thus, preferably the films have no influence on the release of the active ingredient. In the context of the present invention, neither stomach acid-resistant film coatings nor slow-release coatings are used.

Furthermore, the tablet making conditions in the process of the invention are more preferably selected such that the resulting tablets have a tablet depth to weight relationship of 0.005 to 0.3 mm/mg, particularly preferably 0.05 to 0.2 mm/mg.

Further, the resulting tablets preferably have a hardness of 50 to 250 N, particularly preferably 80 to 200 N, in particular 110 to 170 N. The hardness is determined in accordance with Ph Eur 6.0, section 2.9.8.

In addition, the resulting tablets preferably have a friability of less than 5%, particularly preferably less than 3%, in particular less than 2%. The friability is determined in accordance with Ph Eur 6.0, section 2.9.7.

Finally, the tablets of the invention usually have a content uniformity of 90% to 110%, preferably 95% to 105%, in particular 98% to 102% from the mean content. The content uniformity is determined in accordance with Ph Eur 6.0 section 2.9.6.

The second aspect of the invention will now be summarized by the following points:

1. A pharmaceutical intermediate containing a microencapsulated desfesoterodine tartaric acid salt. Reference is hereby made to all of the foregoing discussions regarding preferred embodiments (for example the crystalline R form) of the desfesoterodine tartaric acid salt of the invention.
2. A pharmaceutical intermediate constructed from a core (a) and a shell (b), wherein:
    (a) the core contains a desfesoterodine tartaric acid salt as the active ingredient; and
    (b) the shell contains one or more pharmaceutical excipients which modify release of the active ingredient;
   wherein preferably, the weight ratio of core (a) to shell (b) is 15:1 to 1:5.
3. An intermediate in accordance with point 2, wherein the shell comprises the components:
   (b1), a substance which is not soluble in water, preferably a polymer which is not soluble in water; and
   (b2) a pore-forming agent.
4. An intermediate according to point 3, wherein the shell additionally comprises the components:
   (b3), a polymer with a pH-dependent solubility; and/or
   (b4) a plasticizer.
5. An intermediate according to point 3 or point 4, wherein the shell contains:
   (b1) 75% to 95% by weight of polymer which is not soluble in water;
   (b2) 0.1% to 20% by weight of pore-forming agent and
   (b4) 0 to 20% by weight of plasticizer.
6. An intermediate according to one of points 1 to 5, wherein the intermediate is in the form of a particulate composition and the mass average particle diameter is 0.5 to 5.0 mm.
7. An intermediate according to one of points 1 to 6, wherein the active ingredient is a desfesoterodine tartaric acid salt in the polymorphic R form defined above.
8. A process for the production of a pharmaceutical intermediate according to one of points 1 to 7, comprising the following steps:
   (i) preparing desfesoterodine tartaric acid salt in a particulate form;
   (ii) preparing a solution which contains shell-forming pharmaceutical excipients;
   (iii) spraying the solution from step (ii) onto the particles of desfesoterodine tartaric acid salt; and
   (iv) removing the solvent.
9. A process according to point 8, wherein in step (i), a desfesoterodine tartaric acid salt with a mean particle size of 0.5 to 5.0 mm is used.
10. An intermediate obtainable using a process according to point 8 or point 9.
11. A pharmaceutical formulation containing an intermediate according to one of points 7 to 10 as well as one or more pharmaceutical excipients.
12. A pharmaceutical formulation according to point 11, wherein the quantity of active ingredient is more than 5.0% to 15% by weight with respect to the total formulation weight.

13. A process for the production of a tablet containing a pharmaceutical formulation according to point 11 or point 12, comprising the following steps:
(a) mixing an intermediate according to one of points 1 to 7 and 10 with pharmaceutical excipients;
(b) pressing into tablets, if appropriate with the addition of further pharmaceutical excipients; and
(c) if appropriate, coating the tablets.
14. A tablet with a friability of less than 3%, with a content uniformity of 95% to 105% and with a hardness of 80 to 200 N, containing a pharmaceutical formulation according to point 11 or point 12.
15. A microencapsulated desfesoterodine tartaric acid salt for the treatment of overactive bladder syndrome.

The invention will now be illustrated by means of the following examples.

EXAMPLES

Example 1

Desfesoterodine Tartrate Salt from THF 3.6 g (10.5 μmole) of desfesoterodine (as the free base, produced in accordance with WO 2005/012227) was dissolved in 120.0 mL of THF in a 500 mL flask and heated to 55° C. 1.5 g (10.0 μmole) of L-(+)-tartaric acid dissolved in 60.0 mL of THF was dropped into the solution over 2 hours. After adding ~60% of the L-(+)-tartaric acid, the tartrate salt started to crystallize out. After all of the L-(+)-tartaric acid had been added, the suspension was cooled to room temperature and then stored overnight in the cold (5° C.). Suction was applied to the crystals obtained, they were washed with cold THF and then dried at 50° C./400 mbar for 24 hours. 3.75 g (76.2%) of a white, crystalline solid was obtained.

Example 2

Desfesoterodine Tartrate Salt from 2-Butanone 0.6 g (1.8 μmole) of desfesoterodine (as the free base, produced in accordance with WO 2005/012227) was dissolved in 20.0 mL of THF in a 250 mL flask and heated to 75° C. 0.25 g (1.7 μmole) of L-(+)-tartaric acid dissolved in 10.0 mL of 2-butanone was dropped into the solution over 2 hours. After adding ~30% of the L-(+)-tartaric acid, the tartrate salt started to crystallize out. After all of the L-(+)-tartaric acid had been added, the suspension was slowly cooled to room temperature. Suction was applied to the crystals obtained, they were washed with cold 2-butanone and then dried at 50° C./400 mbar for 24 hours. 0.65 g (79.6%) of a white, crystalline powder was obtained.

Example 3

Recrystallization from THF for Single Crystal Analysis 1 g of the desfesoterodine tartrate salt of Example 1 was suspended in 125 mL of THF and heated to 55° C. until a clear solution was obtained. This solution was cooled slowly to 0° C., suction was applied to the crystals obtained then they were dried (yield 680 mg).

Comparative Example 1

Desfesoterodine Fumarate Salt from THF 0.19 g (1.6 μmole) of fumaric acid was dissolved in 20 mL of THF in a 250 mL flask at 55° C. 0.62 g (1.8 μmole) of desfesoterodine (as the free base, produced in accordance with WO 2005/012227) dissolved in 10 mL of THF was dropped into the solution over 2 hours.

After addition of the desfesoterodine was complete, the suspension was slowly cooled to room temperature. Suction was applied to the crystals obtained, they were washed with cold THF and then dried at 50° C./400 mbar for 24 hours. 0.68 g (91.0%) of a white, crystalline powder was obtained.

Example 4

In Vitro Solubility and Stability on Storage

The in vitro solubility behaviour of fesoterodine fumarate (crystalline, commercially available), desfesoterodine fumarate in accordance with Comparative Example 1 and desfesoterodine tartrate in accordance with Example 1 of the invention was investigated:

| pH | Fesoterodine fumarate | Desfesoterodine fumarate | Desfesoterodine tartrate |
|---|---|---|---|
| 4.5 | Good | Poor | Good |
| 10 | Good | Poor | Good |

Solubility behaviour scale:
poor: <20 mg/ml
average: 20 to 60 mg/ml
good: >60 to 80 mg/ml
very good: >80 mg/ml Further, the stability on storage of desfesoterodine tartrate was determined in a stress test. This showed that desfesoterodine exhibits advantageous stability on storage in both the solid form and in aqueous solution at a pH of 4.5 and at a pH of 10.

Example 5

Microencapsulated Desfesoterodine Tartaric Acid Salt

Core (a):

| | | |
|---|---|---|
| Desfesoterodine tartaric acid salt | 4.00 | 96.85% |
| Aerosil ® | 0.08 | 1.94% |
| Magnesium stearate | 0.05 | 1.21% |

For a batch of 300 g of cores, desfesoterodine tartaric acid salt was mixed with Aerosil® and magnesium stearate for 10 minutes in a gravity mixer (Turbula® T10B) and then pressed into cores on an eccentric press (Korsch® EKO).

The cores contained 4 mg of active ingredient and had a mass average diameter of approximately 2 mm.

300 g of these cores (a) was coated with 145 g of a shell-forming film (b) formed by 77% Aquacoat® ECD (b1), 6% triethyl citrate (b4), 2% polyethylene glycol (b2) and 15% water in a fluidized bed unit (Glatt GPC 3.1).

Next, an intermediate (coated core) was encased in Microcellac® (75% lactose, 25% microcrystalline cellulose) and 1% magnesium stearate and compressed to form tablets with a total weight of 320 mg and a hardness of 150 N (form 12.5×6.5 mm, content 4 mg).

The invention claimed is:
1. A crystalline desfesoterodine salt of tartaric acid that is the polymorphic R form characterized by an X-ray diffracto- gram having reflections at 11.7°±0.2°, 18.4°±0.2° and 18.8°±0.2° on the 2-theta scale with λ,=1.54 Å(Cu K$_a$).

2. The desfesoterodine salt according to claim 1, wherein the salt is a desfesoterodine salt of L-(+)-tartaric acid.

3. The desfesoterodine salt according to claim 1 or claim 2, wherein desfesoterodine and tartaric acid are present in the salt in a molar ratio of desfesoterodine to tartaric acid of approximately 1:1.

4. The desfesoterodine salt according to claim 1, wherein the crystalline form has a crystalline lattice having a laminar structure.

5. The desfesoterodine salt according to claim 1, wherein the crystal form is monoclinic.

6. The desfesoterodine salt according to claim 1, wherein the desfesoterodine salt has a melting point in the range of 166° C. to 170° C.

7. A process for the production of the desfesoterodine salt of tartaric acid according to claim 1 comprising the following steps:
 (i) dissolving desfesoterodine in a first solvent;
 (ii) dissolving tartaric acid in a second solvent;
 wherein the first and the second solvents have a polarity of 0.4 to 0.9 measured at 20° C.;
 (iii) combining the solutions from steps (i) and (ii);
 (iv) allowing the desfesoterodine to crystallize in the form of the tartaric acid salt, optionally, by cooling the solution from step (iii) to temperatures of −50° C. to 15° C.

8. The process according to claim 7, wherein the first and second solvents are identical, and are butanone or tetrahydrofuran.

9. The process according to claim 7 or claim 8, wherein the steps (i) to (iii) are carried out at a temperature of 20° C. to 80° C.

10. The process according to claim 9, further comprising drying the desfesoterodine tartaric acid salt under reduced pressure, wherein the drying conditions are selected such that the desfesoterodine tartaric acid salt has a residual solvent content of less than 2% by weight after drying.

11. A pharmaceutical formulation, comprising the desfesoterodine tartaric acid salt according to claim 1, wherein the pharmaceutical formulation, when taken orally, is bioequivalent to a corresponding pharmaceutical formulation of fesoterodine fumarate or fesoterodine hydrogen fumarate.

12. A pharmaceutical dosage form, comprising a film having a water vapor permeability of 0.1 g/m$^2$d to 2.0 g/m$^2$d, as a package for a pharmaceutical dosage form containing the desfesoterodine tartaric acid salt according to claim 1 for oral administration.

13. A pharmaceutical intermediate constructed from a core (a) and a shell (b), wherein
 (a) the core contains the desfesoterodine tartaric acid salt in accordance with claim 1 as the active ingredient; and
 (b) the shell contains one or more pharmaceutical excipients which modify release of the active ingredient.

14. An oral dosage form containing a pharmaceutical intermediate in accordance with claim 13.

15. The oral dosage form according to claim 14 in the form of a tablet.

* * * * *